US012278007B2

(12) United States Patent
Himeno

(10) Patent No.: US 12,278,007 B2
(45) Date of Patent: Apr. 15, 2025

(54) MEDICINE PRESCRIPTION ASSISTANCE SYSTEM

(71) Applicant: IRYOU JYOUHOU GIJYUTU KENKYUSHO CORPORATION, Fukuoka (JP)

(72) Inventor: Shinkichi Himeno, Yame-gun (JP)

(73) Assignee: IRYOU JYOUHOU GIJYUTU KENKYUSHO CORPORATION, Yame-gun (JP)

( * ) Notice: Subject to any disclaimer, the term of this patent is extended or adjusted under 35 U.S.C. 154(b) by 509 days.

(21) Appl. No.: 17/462,696

(22) Filed: Aug. 31, 2021

(65) Prior Publication Data

US 2021/0398634 A1  Dec. 23, 2021

Related U.S. Application Data

(63) Continuation-in-part of application No. PCT/JP2020/012571, filed on Mar. 23, 2020.

(30) Foreign Application Priority Data

Mar. 26, 2019 (JP) .................................. 2019-058359

(51) Int. Cl.
*G16H 20/10* (2018.01)
*A61B 5/00* (2006.01)
(Continued)

(52) U.S. Cl.
CPC ........... *G16H 20/10* (2018.01); *A61B 5/4848* (2013.01); *G16H 10/60* (2018.01); *G16H 50/70* (2018.01);
(Continued)

(58) Field of Classification Search
CPC ........ G16H 20/10; G16H 70/60; G16H 10/60; G16H 50/70; G16H 70/40; G16H 40/20; A61B 5/4848
See application file for complete search history.

(56) References Cited

U.S. PATENT DOCUMENTS 7,231,606 B2 * 6/2007 Miller ..................... H04L 67/02
702/186
8,700,589 B2 * 4/2014 Tymoshenko ......... G16H 50/70
707/706

(Continued)

FOREIGN PATENT DOCUMENTS

| JP | H08315040 A | 11/1996 |
| JP | 2000298693 A | 10/2000 |

(Continued)

OTHER PUBLICATIONS

Garcia, Elsevier, 2013, pp. 1413-1420.*

(Continued)

*Primary Examiner* — Michael I Ezewoko
(74) *Attorney, Agent, or Firm* — Maier & Maier, PLLC

(57) ABSTRACT

[Problem] To compress the number of records and make consistent records with good visibility by arranging medicine, disease, and symptom/finding entries in a tree structure having a hierarchical structure and recording common attributes in an entry at an appropriate level.
[Solving Means] A medicine prescription assistance system includes medicine information recording means related to medicine entries including medicine names and class names grouping the medicine names. The medicine information recording means each include (1) medicine entry attribute recording means that is recording attributes about the medicine names and the class names grouping the medicine names, (2) medicine entry parent-child relationship link means that defines parent-child relationships between the (Continued)

medicine entries, and (3) medicine information recording means including medicine entry attribute record parent-child inheritance means configured to inherit an attribute recorded in the medicine entry attribute recording means of a parent to the medicine entry attribute recording means of a child through the medicine entry parent-child relationship link means.

18 Claims, 13 Drawing Sheets

(51) Int. Cl.
*G16H 10/60* (2018.01)
*G16H 50/70* (2018.01)
*G16H 70/40* (2018.01)
*G16H 70/60* (2018.01)
*G16H 40/20* (2018.01)

(52) U.S. Cl.
CPC ............ *G16H 70/40* (2018.01); *G16H 70/60* (2018.01); *G16H 40/20* (2018.01)

(56) References Cited

U.S. PATENT DOCUMENTS

| | | | | |
|---|---|---|---|---|
| 11,217,334 B2* | 1/2022 | Netzer | ................... | G16H 70/40 |
| 11,250,856 B2* | 2/2022 | Montyne | ................ | G16H 15/00 |
| 2007/0088559 A1 | 4/2007 | Kim | | |
| 2020/0320405 A1* | 10/2020 | Himeno | ................... | G06N 5/02 |

FOREIGN PATENT DOCUMENTS

| | | |
|---|---|---|
| JP | 2003024416 A | 1/2003 |
| JP | 2003308392 A | 10/2003 |
| JP | 2004110532 A | 4/2004 |
| JP | 2006158490 A | 6/2006 |
| JP | 2008083928 A | 4/2008 |
| JP | 2008250415 A | 10/2008 |
| JP | 2011180927 A | 9/2011 |
| JP | 2012074002 A | 4/2012 |
| JP | 2012133564 A | 7/2012 |
| JP | 2016021081 A | 2/2016 |
| JP | 2018081528 A | 5/2018 |
| JP | 2019032732 A | 2/2019 |
| JP | 2019101517 A | 6/2019 |
| WO | 2016/103322 A1 | 6/2016 |

OTHER PUBLICATIONS

International Search Report issued on Jun. 30, 2020 in corresponding International Application No. PCT/JP2020/012571; 4 pages.
Notice of Reasons for Refusal issued on Nov. 11, 2019 in corresponding Japanese Application No. 2019-058359; 9 pages.

* cited by examiner

Fig. 10

WARFARIN

<ADAPTATION DISEASE>

| | FREQUENCY |
|---|---|
| PHLEBOTHROMBOSIS | 58 |
| MYOCARDIAL THROMBOSIS | 50 |
| LUNG SAC | 45 |
| ⋮ | ⋮ |

<EFFICACY/EFFECTIVENESS SYMPTOM/FINDING>

| | FREQUENCY |
|---|---|
| LOWER LIMBS COLDNESS | 20 |
| FOUR LIMBS NUMBNESS | 15 |
| ⋮ | ⋮ |

<SIDE-EFFECT SYMPTOM/FINDING>

| | FREQUENCY |
|---|---|
| SUBCUTANEOUS BLEEDING | 58 |
| HEMATEMESIS | 5 |
| ANAEMIA | 1 |
| ⋮ | ⋮ |

Fig. 11

FOUR LIMBS COLDNESS

<EFFICACY/EFFECTIVENESS MEDICINE>
|  | FREQUENCY |
|---|---|
| OPALMON | 108 |
| AMPLAG | 58 |
| WARFARIN | 40 |
| ⋮ | ⋮ |

<SIDE-EFFECT MEDICINE>
|  | FREQUENCY |
|---|---|
| 5FU | 52 |
| INOVAN | 10 |
| ⋮ | ⋮ |

Fig. 12

WARFARIN
.
.
.

<SIDE-EFFECT SYMPTOM/FINDING>

|  |  | FREQUENCY |
|---|---|---|
| SUBCUTANEOUS BLEEDING |  | 58 |
| COMBINED USE MEDICINE | BAYASPIRIN | 25 |
|  | AMLODIN | 18 |
|  | . | |
|  | . | |
|  | . | |
| HEMATEMESIS |  | 5 |
| COMBINED USE MEDICINE | ATRTAUT | 2 |
|  | S · M COMBINATION POWDER | 1 |

<SIDE-EFFECT MEDICINE>

|  |  |  | FREQUENCY |
|---|---|---|---|
| 5FU |  |  | 52 |
|  | COMBINED USE MEDICINE | FOLIAMIN | 25 |
|  |  | PRIMPERAN | 18 |

⋮

| INOVAN |  |  | 10 |
|---|---|---|---|
|  | COMBINED USE MEDICINE | FUROSEMIDE | 3 |
|  |  | OPALMON | 2 |

⋮

MEDICINE PRESCRIPTION ASSISTANCE SYSTEM

TECHNICAL FIELD

The present invention relates to a system that assists a doctor who issues prescriptions at a medical site by providing information on the usage and dosage, efficacy, side effect, and the like.

BACKGROUND ART

When issuing a prescription corresponding to the state of a patient at a medical site, a doctor determines an appropriate medicine whose efficacy can be expected by comprehensively considering the disease name, symptoms, and findings, such as blood test data, of the patient. At this time, the doctor needs not only information on the usage, dosage, and efficacy of the prescribed medicine but also detailed information on diseases, symptoms, and findings against which the medicine is prohibited from being prescribed, possible side effects, and the like.

The disease name, symptoms, and findings of a patient are described on a medical record. Electronic patient records (electronic medical records) have been widely used in recent year. Each medicine has adaptation diseases and efficacy/effectiveness (symptoms and findings against which the medicine has efficacy and effectiveness), usage and dosage, diseases, symptoms, and findings to which caution should be taken when the medicine is prescribed, diseases, symptoms, and findings against which the medicine is prohibited from being prescribed, and others. These are described on book manuals, electronic medical record manuals, and others.

A doctor estimates the name or condition of the disease of a patient from the symptoms and findings of the patient on a medical record and prescribes a medicine that has efficacy and effectiveness against the disease name, symptoms, and findings. At this time, the doctor needs to take into account diseases, symptoms, and findings against which this medicine is prohibited from being prescribed, possible side effects, and the like.

As described above, each medicine has adaptation diseases and efficacy/effectiveness (symptoms and findings against which the medicine has efficacy and effectiveness), usage and dosage, diseases, symptoms, and findings to which caution should be taken when the medicine is prescribed, diseases, symptoms, and findings against which the medicine is prohibited from being prescribed, and others, and these pieces of information are provided in a list form. Doctors have read such listed information on each medicine and prescribed medicines.

Background art literature relating to the present application includes the following.

CITATION LIST

Patent Literature

Patent Literature 1: Japanese Unexamined Patent Application Publication No. 2012-133564

SUMMARY OF INVENTION

Technical Problem

Medicine information, disease information, and symptoms and findings have been described independently. For this reason, the description of such information tends to become enormous in amount and lacks good visibility. Also, there are many overlapping descriptions. When some descriptions have to be changed due to the progress of medicine, it takes much effort to maintain the consistency since such descriptions are scattered.

It takes time to fully list disease names, symptoms, and findings to be treated, from patient information records, and failures to list all such descriptions have sometimes resulted in medical accidents.

At the present time, when new medicines and generic medicines are being drastically increased, it is becoming difficult to appropriately list adaptation medicines. Also, it is unexpectedly difficult to distinguish between symptoms and findings acting as diseases and symptoms and findings that may be side effects. Also, while it is important to early find a medicine that may be causing a side effect, it is difficult to determine such a medicine on the spot.

In selecting a medicine, it is useful to know the past prescription tendency. However, in the case of conventional medicine information or disease information, disease names, symptoms, and findings are often simply listed and therefore it is difficult to determine the tendency or importance. Also, information on the side effects of medicines is mostly that in the clinical trial stage, where the medicines have yet to be put on the market, and information on side effects that occur when the medicines are prescribed for actual patients having various backgrounds is small in amount under the present circumstances.

In particular, there is actually almost no information on side effects based on the interaction between multiple medicines used in combination.

The present invention has been made to solve the problems with the background art, and an object thereof is to provide a system that compresses the number of records and makes consistent records with good visibility by arranging medicine entries, disease entries, and symptom/finding entries in a tree structure having a hierarchical structure and recording common attributes in an entry at an appropriate level together, as well as alleviates the above difficulties at clinical sites by utilizing the entries as terms in other entry attributes through reference link means, for example, recommends an appropriate medicine, checks the usage, dosage, and prescription conditions, or points out omission of a disease name (if any) in patient information records using these pieces of information. Another object thereof is to provide a system that assists doctors in determinations by counting up the frequencies of disease names, medicine names, corresponding symptoms and findings, side effects, and the like each time they are confirmed and presenting disease names, medicine names, corresponding symptoms and findings, side effects, and the like in the descending order of frequency when the doctors make reference on the spot to prescribe a medicine, as well as assists the solution of problems with prescription of multiple medicines by recording the frequencies of symptoms and findings, side effects, and the like when using medicines in combination.

Solution to Problem

As means for accomplishing the above objects, a medicine prescription assistance system includes medicine information recording means related to medicine entries including medicine names and class names grouping the medicine names. The medicine information recording means each include (1) medicine entry attribute recording means that is recording attributes about the medicine names and the class names grouping the medicine names, (2) medicine entry parent-child relationship link means that defines parent-child relationships between the medicine entries, and (3) medicine entry attribute record parent-child inheritance means configured to inherit an attribute recorded in the medicine entry attribute recording means of a parent to the medicine entry attribute recording means of a child through the medicine entry parent-child relationship link means.

According to the medicine prescription assistance system, the medicine prescription assistance system includes disease information recording means related to disease entries including disease names and class names grouping the disease names. The disease information recording means each includes (1) disease entry attribute recording means that is recording attributes about the disease names and the class names grouping the disease names, (2) disease entry parent-child relationship link means that defines parent-child relationships between the disease entries, and (3) disease entry attribute record parent-child inheritance means configured to inherit an attribute recorded in the disease entry attribute recording means of a parent to the disease entry attribute recording means of a child through the disease entry parent-child relationship link means. The medicine prescription assistance system includes reference link means through which the disease entries are referenced as terms in the medicine entry attribute recording means or the medicine entries are conversely referenced as terms in the disease entry attribute recording means.

According to the medicine prescription assistance system, the medicine prescription assistance system includes symptom/finding information recording means related to symptom and finding entries including symptom and finding names and class names grouping the symptom and finding names. The symptom/finding information recording means each include (1) symptom/finding entry attribute recording means that is recording attributes about the symptom and finding names and the class names grouping the symptom and finding names, (2) symptom/finding entry parent-child relationship link means that defines parent-child relationships between the symptom entries or the finding entries, and (3) symptom/finding entry attribute record parent-child inheritance means configured to inherit an attribute recorded in the symptom/finding entry attribute recording means of a parent to the symptom/finding entry attribute recording means of a child through the symptom/finding entry parent-child relationship link means. The medicine prescription assistance system includes reference link means through which the symptom and finding entries, the disease entries, and the medicine entries are mutually referenced as terms in the medicine entry attribute recording means, the disease entry attribute recording means, and the symptom/finding entry attribute recording means.

According to the medicine prescription assistance system 4, in the medicine prescription assistance system, the medicine entry attribute recording means includes prescribable condition recording means that is recording a condition under which a medicine is allowed to be prescribed and medicine prescription condition conformity check means configured to, when the medicine is prescribed to a patient, check whether a patient information record of the patient conforms to the condition and to, if the patient information record does not conform to the condition, issues an warning to a prescribing person.

According to the medicine prescription assistance system 5, in the medicine prescription assistance system, the medicine entry attribute recording means includes usage/dosage recording means that is recording prescribable usage and dosage of a medicine and medicine usage/dosage check means configured to, when the medicine is prescribed to a patient, check whether usage and dosage of the medicine conform to the prescribable usage and dosage while referencing a patient information record of the patient as necessary and to, if the usage and dosage do not conform to the prescribable usage and dosage, issue a warning to a prescribing person.

According to the medicine prescription assistance system 6, in the medicine prescription assistance system, the medicine entry attribute recording means includes adaptation disease name list recording means that is recording a list of adaptation disease names against which a medicine is allowed to be prescribed and medicine adaptation disease name check means configured to, when the medicine is prescribed to a patient, check whether there is an adaptation disease name in a patient information record of the patient and to, if there is no adaptation disease name, urge a prescribing person to input an adaptation disease.

According to the medicine prescription assistance system 7, in the medicine prescription assistance system, the disease entry attribute recording means includes adaptation medicine name list recording means that is recording a list of adaptation medicine names against a disease and disease adaptation medicine list presentation means configured to present a list of medicines that are allowed to be prescribed to a patient of the disease through the reference link means.

According to the medicine prescription assistance system 8, in the medicine prescription assistance system, the medicine entry attribute recording means includes contraindication disease name list recording means that is recording a list of contraindication disease names that contraindicate a medicine and medicine contraindication disease name check means configured to, when the medicine is prescribed to a patient, check whether there is a contraindication disease name in a patient information record of the patient through the reference link means.

According to the medicine prescription assistance system 9, in the medicine prescription assistance system, the medicine entry attribute recording means includes contraindication symptom/finding list recording means that is recording a list of contraindication symptoms and findings that contraindicate a medicine and medicine contraindication symptom/finding check means configured to, when the medicine is prescribed to a patient, check whether there is a contraindication symptom or finding in a patient information record of the patient through the reference link means.

According to the medicine prescription assistance system 10, in the medicine prescription assistance system, the medicine entry attribute recording means includes efficacy/effectiveness symptom/finding recording means that is recording a list of symptoms and findings against which a medicine has efficacy and effectiveness and medicine efficacy/effectiveness symptom/finding check means configured to, when the medicine is prescribed to a patient, check whether there is a symptom or finding against which the medicine has efficacy and effectiveness, in a patient information record of the patient through the reference link means.

According to the medicine prescription assistance system 11, the medicine prescription assistance system, the symptom/finding entry attribute recording means includes efficacy/effectiveness medicine name list recording means that is recording a list of medicine names that have efficacy and effectiveness against a symptom or finding and symptom/finding-specific efficacy/effectiveness medicine list presentation means configured to present a list of medicines that have efficacy and effectiveness for a patient having the symptom or finding through the reference link means.

According to the medicine prescription assistance system 12, in the medicine prescription assistance system, the medicine entry attribute recording means includes side-effect symptom/finding list recording means that is recording a list of side-effect symptoms and findings that may be caused by a medicine and medicine side-effect symptom/finding check means configured to, when the medicine is prescribed to a patient, check whether there is a side-effect symptom or finding in a patient information record of the patient through the reference link means.

According to the medicine prescription assistance system 13, in the medicine prescription assistance system, the symptom/finding entry attribute recording means includes side-effect medicine name list recording means that is recording a list of medicine names that may cause a symptom or finding as a side effect and symptom/finding side effect medicine list presentation means configured to present a list of medicines that may cause a side effect, to a medicine prescription list of a patient having the symptom or finding through the reference link means.

According to the medicine prescription assistance system 14, in the medicine prescription assistance system, the adaptation disease name list recording means of the medicine entry attribute recording means includes disease-specific medicine prescription frequency recording means that is recording frequencies with which a medicine has been prescribed against diseases and frequency descending order medicine adaptation disease name display means configured to, when a disease name corresponding to medicine names is confirmed, count up the disease-specific prescription frequency recording means and to, when the medicine is prescribed next time, display a list of adaptation disease names in the descending order of the frequencies of prescription.

According to the medicine prescription assistance system 15, in the medicine prescription assistance system, the adaptation medicine name list recording means of the disease entry attribute recording means includes medicine-specific prescription frequency recording means that is recording frequencies with which medicines have been prescribed against a disease and frequency descending order disease adaptation medicine name presentation means configured to, when a disease name corresponding to medicine names is confirmed, count up the medicine-specific prescription frequency recording means and to, when a medicine is prescribed against the disease next time, present a list of adaptation medicine names in the descending order of the frequencies of prescription.

According to the medicine prescription assistance system 16, in the medicine prescription assistance system, the efficacy/effectiveness symptom/finding list recording means of the medicine entry attribute recording means includes efficacy/effectiveness-specific prescription frequency recording means that is recording frequencies with which the medicine has been prescribed against efficacy/effectiveness symptoms and findings and frequency descending order medicine efficacy/effectiveness symptom/finding presentation means configured to, when a efficacy/effectiveness symptom or finding corresponding to medicine names is confirmed, count up the efficacy/effectiveness symptom/finding-specific prescription frequency recording means and to, when the medicine is prescribed next time, present a list of efficacy/effectiveness symptoms and findings in the descending order of the frequencies of prescription.

According to the medicine prescription assistance system 17, in the medicine prescription assistance system, the efficacy/effectiveness medicine name list recording means of the symptom/finding entry attribute recording means includes efficacy/effectiveness symptom/finding-specific medicine prescription frequency recording means that is recording frequencies with which medicines have been prescribed against the efficacy/effectiveness symptom or finding and frequency descending order efficacy/effectiveness symptom/finding medicine display means configured to, when a efficacy/effectiveness symptom or finding corresponding to medicine names is confirmed, count up the efficacy/effectiveness symptom/finding-specific medicine prescription frequency recording means and, when a medicine is prescribed against the efficacy/effectiveness symptom or finding next time, display a list of medicine names in the descending order of the frequencies of prescription.

According to the medicine prescription assistance system 18, in the medicine prescription assistance system, the side-effect symptom/finding list recording means of the medicine entry attribute recording means includes side-effect symptom/finding-specific prescription frequency recording means that is recording frequencies with which the medicine has been prescribed against side-effect symptoms and findings and frequency descending order medicine side-effect symptom/finding presentation means configured to, when prescription of the medicine against a side-effect symptom/finding corresponding to medicine names is confirmed, count up the side-effect symptom/finding-specific prescription frequency recording means and, when the medicine is prescribed next time, present a list of side-effect symptoms and findings in the descending order of the frequencies of prescription.

According to the medicine prescription assistance system 19, in the medicine prescription assistance system, the side-effect symptom/finding list recording means of the medicine entry attribute recording means includes side-effect symptom/finding-specific combined use medicine combination prescription frequency recording means that is recording frequencies with which the medicine and combined use medicines have been prescribed in combination against side-effect symptoms and findings and combined use medicine combination frequency descending order medicine side-effect symptom/finding presentation means configured to, when prescription of the medicine against a side-effect symptom/finding corresponding to medicine names is confirmed, count up the side-effect symptom/finding-specific combined use medicine combination prescription frequency recording means and to, when there is a combined use medicine when prescribing the medicine next time, present a list of side-effect symptoms and findings in the descending order of the frequencies of combined use medicine combination prescription.

According to the medicine prescription assistance system 20, in the medicine prescription assistance system, the side-effect medicine name list recording means of the symptom/finding entry attribute recording means includes side-effect symptom/finding medicine prescription frequency recording means that is recording frequencies with which medicines have been prescribed against the side-effect symptom or finding and frequency descending order side-effect symptom/finding medicine presentation means configured to, when prescription of the medicine against a side-effect symptom/finding corresponding to medicine names is confirmed, count up the side-effect symptom/finding medicine prescription frequency recording means and to, when considering involvement of a medicine in the side-effect symptom or finding next time, present a list of medicine names in the descending order of the frequencies of prescription.

According to the medicine prescription assistance system 21, in the medicine prescription assistance system, the side-effect medicine name list recording means of the symptom/finding entry attribute recording means includes side-effect symptom/finding combined use medicine combination prescription frequency recording means that is recording frequencies with which medicines and combined use medicines have been prescribed in combination against the side-effect symptom or finding and combined use side-effect symptom/finding medicine combination frequency descending order medicine presentation means configured to, when prescription of the medicine against a side-effect symptom/finding corresponding to medicine names is confirmed, count up the side-effect symptom/finding combined use medicine combination prescription frequency recording means and to, when there is a combined use medicine when considering involvement of a medicine to the side effect symptom or finding next time, present a list of medicine names in the descending order of the frequencies of combined use medicine combination prescription.

Advantageous Effectiveness of Invention

The medicine prescription assistance system includes the medicine entry attribute recording means and thus is recording the attributes about the medicine names and the class names grouping the medicine names.

The medicine prescription assistance system also includes the medicine entry parent-child relationship link means and thus defines the parent-child relationships between the medicine entries.

The medicine prescription assistance system also includes the medicine information recording means including the medicine entry attribute record parent-child inheritance means configured to inherit the attribute recorded in the medicine entry attribute recording means of the parent to the medicine entry attribute recording means of the child through the medicine entry parent-child relationship link means.

The medicine prescription assistance system includes the disease entry attribute recording means and thus is recording the attributes about the disease names and the class names grouping the disease names.

The medicine prescription assistance system also includes the disease entry parent-child relationship link means and thus defines the parent-child relationships between the disease entries.

The medicine prescription assistance system also includes the disease information recording means including the disease entry attribute record parent-child inheritance means and thus inherits the attribute recorded in the disease entry attribute recording means of the parent to the disease entry attribute recording means of the child through the disease entry parent-child relationship link means.

The medicine prescription assistance system also includes the reference link means and thus the disease entries are referenced as terms in the medicine entry attribute recording means or the medicine entries are conversely referenced as terms in the disease entry attribute recording means.

The medicine prescription assistance system includes the symptom/finding entry attribute recording means and thus is recording the attributes about the symptom and finding names and the class names grouping the symptom and finding names.

The medicine prescription assistance system also includes the symptom/finding entry parent-child relationship link means and thus defines parent-child relationships between the symptom entries or the finding entries.

The medicine prescription assistance system also includes the symptom/finding information recording means including the symptom/finding entry attribute record parent-child inheritance means and thus inherits the attribute recorded in the symptom/finding entry attribute recording means of the parent to the symptom/finding entry attribute recording means of the child through the symptom/finding entry parent-child relationship link means.

The medicine prescription assistance system also includes the reference link means and thus the symptom and finding entries, the disease entries, and the medicine entries are mutually referenced as terms in the medicine entry attribute recording means, the disease entry attribute recording means, and the symptom/finding entry attribute recording means.

The medicine prescription assistance system includes the prescribable condition recording means and thus is recording the condition under which the medicine corresponding to the medicine entry attribute recording means is allowed to be prescribed.

The medicine prescription assistance system also includes the medicine prescription condition conformity check means and thus, when prescribing the medicine to a patient, checks whether a patient information record of the patient conforms to the condition and, if the patient information record does not conform to the condition, issues a warning to a prescribing person.

The medicine prescription assistance system includes the usage/dosage recording means and thus is recording the prescribable usage and dosage of the medicine corresponding to the medicine entry attribute recording means.

The medicine prescription assistance system also includes the medicine usage/dosage check means and thus, when the medicine is prescribed to a patient, checks whether the usage and dosage of the medicine conform to the prescribable usage and dosage while referencing a patient information record of the patient as necessary and, if the usage and dosage do not conform to the prescribable usage and dosage, issue a warning to a prescribing person.

The medicine prescription assistance system includes the adaptation disease name list recording means and thus is recording the list of adaptation disease names against which the medicine corresponding to the medicine entry attribute recording means is allowed to be prescribed.

The medicine prescription assistance system also includes the medicine adaptation disease name check means and thus, when the medicine is prescribed to a patient, checks whether there is an adaptation disease name in a patient information record of the patient and, if there is no adaptation disease name, urge a prescribing person to input an adaptation disease.

The medicine prescription assistance system includes the adaptation medicine name list recording means and thus is recording the list of adaptation medicine names against the disease corresponding to the disease entry attribute recording means.

The medicine prescription assistance system also includes the disease adaptation medicine list presentation means and thus presents a list of medicines that are allowed to be prescribed to a patient of the disease through the reference link means.

The medicine prescription assistance system includes the contraindication disease name list recording means and thus is recording the list of contraindication disease names that contraindicate the medicine corresponding to the medicine entry attribute recording means.

The medicine prescription assistance system also includes the medicine contraindication disease name check means and thus, when the medicine is prescribed to a patient, checks whether there is a contraindication disease name in a patient information record of the patient through the reference link means.

The medicine prescription assistance system includes the contraindication symptom/finding list recording means and thus is recording the list of contraindication symptoms and findings that contraindicate the medicine corresponding to the medicine entry attribute recording means.

The medicine prescription assistance system also includes the medicine contraindication symptom/finding check means and thus, when the medicine is prescribed to a patient, checks whether there is a contraindication symptom or finding in a patient information record of the patient through the reference link means.

The medicine prescription assistance system includes the efficacy/effectiveness symptom/finding recording means and thus is recording the list of symptoms and findings against which the medicine corresponding to the medicine entry attribute recording means has efficacy and effectiveness.

The medicine prescription assistance system also includes the medicine efficacy/effectiveness symptom/finding check means and thus, when the medicine is prescribed to a patient, checks whether there is a symptom or finding against which the medicine has efficacy and effectiveness, in a patient information record of the patient through the reference link means.

The medicine prescription assistance system includes the efficacy/effectiveness medicine name list recording means and thus is recording the list of medicine names that have efficacy and effectiveness against the symptom or finding corresponding to the symptom/finding entry attribute recording means.

The medicine prescription assistance system also includes the symptom/finding-specific efficacy/effectiveness medicine list presentation means and thus presents the list of medicines that have efficacy and effectiveness for a patient having the symptom or finding through the reference link means.

The medicine prescription assistance system includes the side-effect symptom/finding list recording means and thus is recording the list of side-effect symptoms/findings that may be caused by the medicine corresponding to the medicine entry attribute recording means.

The medicine prescription assistance system also includes the medicine side-effect symptom/finding check means and thus, when the medicine is prescribed to a patient, check whether there is a side-effect symptom or finding in a patient information record of the patient through the reference link means.

The medicine prescription assistance system includes the side-effect medicine name list recording means and thus is recording the list of medicine names that may cause the symptom or finding corresponding to the symptom/finding entry attribute recording means as a side effect.

The medicine prescription assistance system also includes the symptom/finding side-effect medicine list presentation means and thus presents the list of medicines that may cause a side effect, to a medicine prescription list of a patient having the symptom or finding through the reference link means.

The medicine prescription assistance system includes the disease-specific medicine prescription frequency recording means and thus is recording the frequencies with which the medicine corresponding to the medicine entry attribute recording means has been prescribed against diseases.

The medicine prescription assistance system also includes the frequency descending order medicine adaptation disease name display means and thus, when a disease name corresponding to medicine names is confirmed, counts up the disease-specific prescription frequency recording means and, when the medicine is prescribed next time, displays the list of adaptation disease names in the descending order of the frequencies of prescription.

The medicine prescription assistance system includes the medicine-specific prescription frequency recording means and thus is recording the frequencies with which medicines have been prescribed against the disease corresponding to the disease entry attribute recording means.

The medicine prescription assistance system also includes the frequency descending order disease adaptation medicine name presentation means and thus, when a disease name corresponding to medicine names is confirmed, counts up the medicine-specific prescription frequency recording means and, when a medicine is prescribed against the disease next time, presents the list of adaptation medicine names in the descending order of the frequencies of prescription.

The medicine prescription assistance system includes the efficacy/effectiveness-specific prescription frequency recording means and thus is recording the frequencies with which the medicine has been prescribed against efficacy/effectiveness symptoms and findings.

The medicine prescription assistance system also includes the frequency descending order medicine efficacy/effectiveness symptom/finding presentation means and thus, when a efficacy/effectiveness symptom or finding corresponding to medicine names is confirmed, counts up the efficacy/effectiveness symptom/finding-specific prescription frequency recording means and to, when the medicine is prescribed next time, presents the list of efficacy/effectiveness symptoms and findings in the descending order of the frequencies of prescription.

The medicine prescription assistance system includes the efficacy/effectiveness symptom/finding-specific medicine prescription frequency recording means and thus is recording the frequencies with which medicines have been prescribed against the efficacy/effectiveness symptom or finding corresponding to the symptom/finding entry attribute recording means.

The medicine prescription assistance system also includes the frequency descending order efficacy/effectiveness symptom/finding medicine display means and thus, when a efficacy/effectiveness symptom or finding corresponding to medicine names is confirmed, counts up the efficacy/effectiveness symptom/finding-specific medicine prescription frequency recording means and, when a medicine is prescribed against the efficacy/effectiveness symptom or finding next time, displays the list of medicine names in the descending order of the frequencies of prescription.

The medicine prescription assistance system includes the side-effect symptom/finding-specific prescription frequency recording means and thus is recording the frequencies with which the medicine has been prescribed against side-effect symptoms and findings.

The medicine prescription assistance system also includes the frequency descending order medicine side-effect symptom/finding presentation means and thus, when prescription of the medicine against a side-effect symptom/finding corresponding to medicine names is confirmed, counts up the side-effect symptom/finding-specific prescription frequency recording means and, when the medicine is prescribed next time, presents the list of side-effect symptoms and findings in the descending order of the frequencies of prescription.

The medicine prescription assistance system includes the side-effect symptom/finding-specific combined use medicine combination prescription frequency recording means and thus is recording the frequencies with which the medicine and the combined use medicine have been prescribed in combination against side-effect symptoms and findings.

The medicine prescription assistance system also includes the combined use medicine combination frequency descending order medicine side-effect symptom/finding presentation means and thus, when prescription of the medicine against a side-effect symptom/finding corresponding to medicine names is confirmed, counts up the side-effect symptom/finding-specific combined use medicine combination prescription frequency recording means and, when there is a combined use medicine when prescribing the medicine next time, presents the list of side-effect symptoms and findings in the descending order of the frequencies of combined use medicine combination prescription.

The medicine prescription assistance system includes the side-effect symptom/finding medicine prescription frequency recording means and thus is recording the frequencies with which medicines have been prescribed against the side-effect symptom or finding.

The medicine prescription assistance system also includes the frequency descending order side-effect symptom/finding medicine presentation means and thus, when prescription of the medicine against a side-effect symptom/finding corresponding to medicine names is confirmed, counts up the side-effect symptom/finding medicine prescription frequency recording means and, when considering involvement of a medicine in the side-effect symptom or finding next time, presents the list of medicine names in the descending order of the frequencies of prescription.

The medicine prescription assistance system includes the side-effect symptom/finding combined use medicine combination prescription frequency recording means and thus is recording the frequencies with which medicines and combined use medicines have been prescribed in combination against the side-effect symptom or finding.

The medicine prescription assistance system also includes the combined use side-effect symptom/finding medicine combination frequency descending order medicine presentation means and thus, when prescription of the medicine against a side-effect symptom/finding corresponding to medicine names is confirmed, counts up the side-effect symptom/finding combined use medicine combination prescription frequency recording means and, when there is a combined use medicine when considering involvement of a medicine to the side-effect symptom/finding next time, presents the list of medicine names in the descending order of the frequencies of combined use medicine combination prescription.

BRIEF DESCRIPTION OF THE DRAWINGS

FIG. 10 is a diagram showing adaptation disease-specific prescription frequency recording means, efficacy/effectiveness symptom/finding-specific prescription frequency recording means, and side-effect symptom/finding-specific prescription frequency recording means in the medicine entry attribute recording means.

FIG. 11 is a diagram showing efficacy/effectiveness-specific medicine prescription frequency recording means and side effect-specific prescription frequency recording means in the symptom/finding entry attribute recording means.

FIG. 12 is a diagram showing side-effect symptom/finding-specific combined use medicine combination prescription frequency recording means in the medicine entry attribute recording means.

FIG. 13 is a diagram showing side-effect symptom/finding-specific combined use medicine combination prescription frequency recording means in the symptom/finding entry attribute recording means.

DESCRIPTION OF EMBODIMENTS

The medicine prescription assistance system includes the server apparatus, the database and the terminal. The server apparatus, the database and the terminal connected through network. The server apparatus is a prior computer. The server apparatus includes: an arithmetic apparatus including the processor, a main storage apparatus, an auxiliary storage apparatus, input apparatus, output apparatus, and communication apparatus. The arithmetic apparatus, the main storage apparatus, the auxiliary storage apparatus, input apparatus, output apparatus, the communication apparatus connected through a bus interface. The arithmetic apparatus includes the processor that can execute an instruction set. The main storage apparatus includes a volatile memory such as a random access memory (RAM). The auxiliary storage apparatus includes a recording medium such as a nonvolatile memory, and a recording method thereof is not limited. The recording medium indicates a hard disk drive (HDD) or a solid state drive (SSD), for example. The input apparatus is, for example, a keyboard device. The output apparatus includes, for example, display as a liquid crystal panel. The communication apparatus is a network interface that can connect to network. The processor of the server apparatus executes the function of the units of the medicine prescription assistance system including: a class data acquisition means, disease information recording means, medicine entry attribute recording means, medicine entry parent-child relationship link means, medicine entry attribute record parent-child inheritance means or the like. The database is composed of the auxiliary storage apparatus of the server apparatus or the auxiliary storage apparatus independent from the server apparatus. The database stores information managed by the medicine prescription assistance system. The terminal is a prior computer including a processor.

Figure 1:
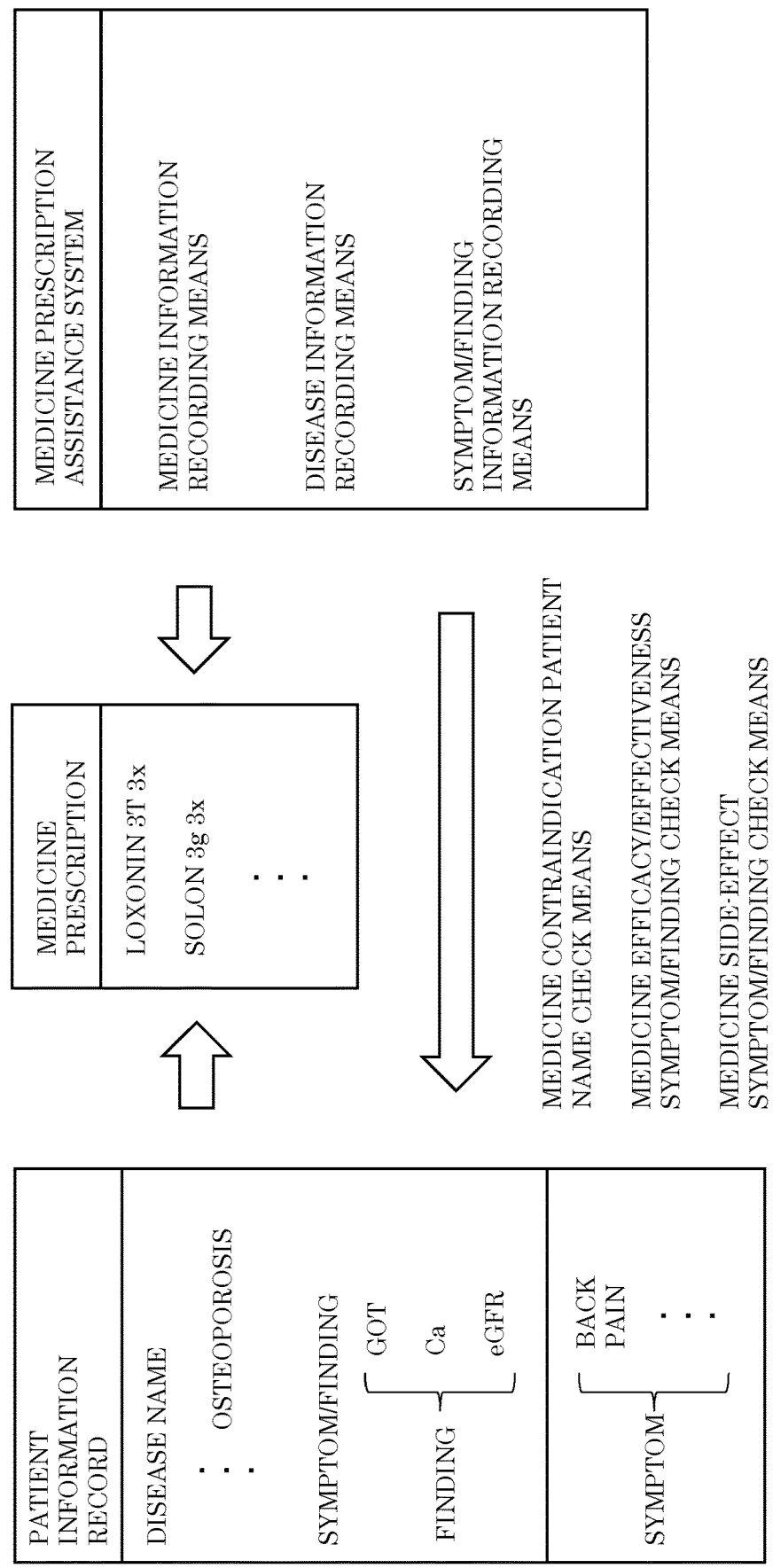
FIG. 1 is a diagram showing the overall structure of a medicine prescription assistance system according to the present invention.

FIG. 1 is a diagram showing the overall structure of a medicine prescription assistance system according to the present invention.

A patient information record is recording, as a medical record, the disease name, symptoms such as pain and numbness, and findings (findings for symptom) in a blood test, CT or MRI examination, or the like of a patient.

A doctor prescribes a medicine for treatment on the basis of patient information. The medicine prescription assistance system evaluates medicine prescription using medicine information recording means that is recording the efficacy, side effects, and the like of medicines, disease information recording means that is recording the symptoms and findings, adaptation medicines, and the like of diseases, symptom/finding information recording means that provides terms to the medicine information recording means and disease information recording means through reference means, or the like.

If there is a shortage of information required for evaluation, the medicine prescription assistance system makes an inquiry to a patient information record using medicine contraindication disease name check means, medicine efficacy/effectiveness symptom/finding check means, medicine side-effect symptom/finding check means, or the like as necessary.

To automatically make an inquiry to a patient information record using the medicine contraindication disease check means, medicine efficacy/effectiveness symptom/finding check means, medicine side-effect symptom/finding check means, or the like, it is, of course, preferred to digitize patient information records and prescriptions (electronic medical records). However, even if conventional paper medical records are being used, the medicine prescription assistance system according to the present invention works if a doctor, pharmacist, or the like manually responds to the inquiry.

Figure 2:
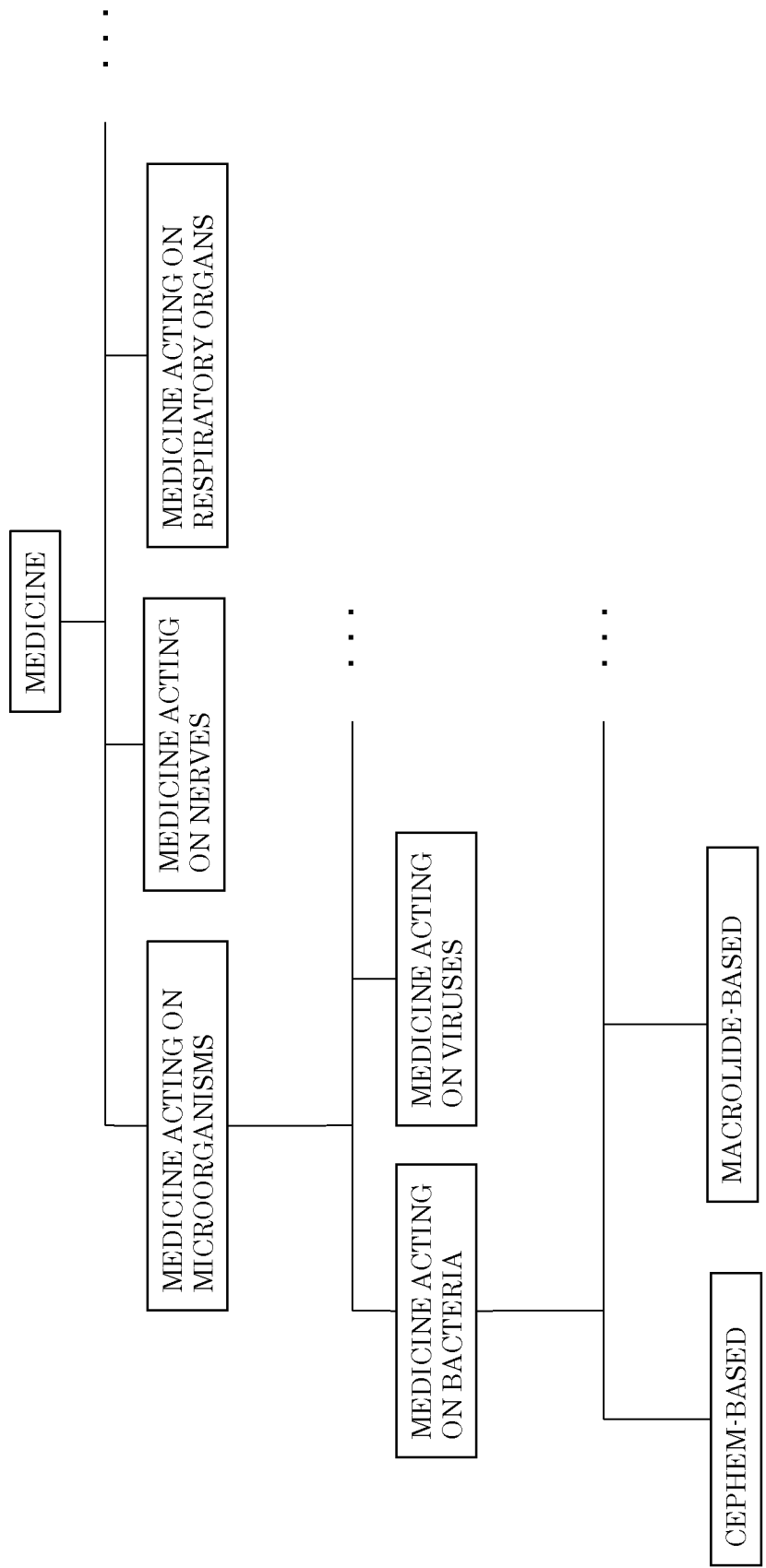
FIG. 2 is a diagram showing medicine information recording means.

FIG. 2 is a diagram showing the medicine information recording means.

Many medicine names and class names grouping the medicine names (medicine entries) are recorded in a tree structure.

Each medicine entry is recording the attributes thereof (medicine entry attribute recording means). Also, the medicine entries are connected by links representing the parent-child relationships between the medicine entries (medicine entry parent-child relationship link means) in a tree structure so that the attributes recorded in the medicine entry attribute recording means of a parent are inherited to the medicine entry attribute recording means of a child (medicine entry attribute record parent-child inheritance means). Thus, it is only necessary to record the common attributes of the medicine entries in a collected manner once.

As a result, the records of the attributes of the medicine entries are structured. That is, complete records are made in the minimum number. Although each medicine entry is recording only the minimum number of attributes, it is able to inherit complete attribute records from the parent thereof as necessary.

Thus, even if any attribute is changed due to, for example, the advancement of medicine, it is only necessary to change the description of the attribute. This change is automatically reflected on the child medicine entries by the medicine entry attribute record parent-child inheritance means. Thus, the consistency of the descriptions is easily maintained.

Figure 3:
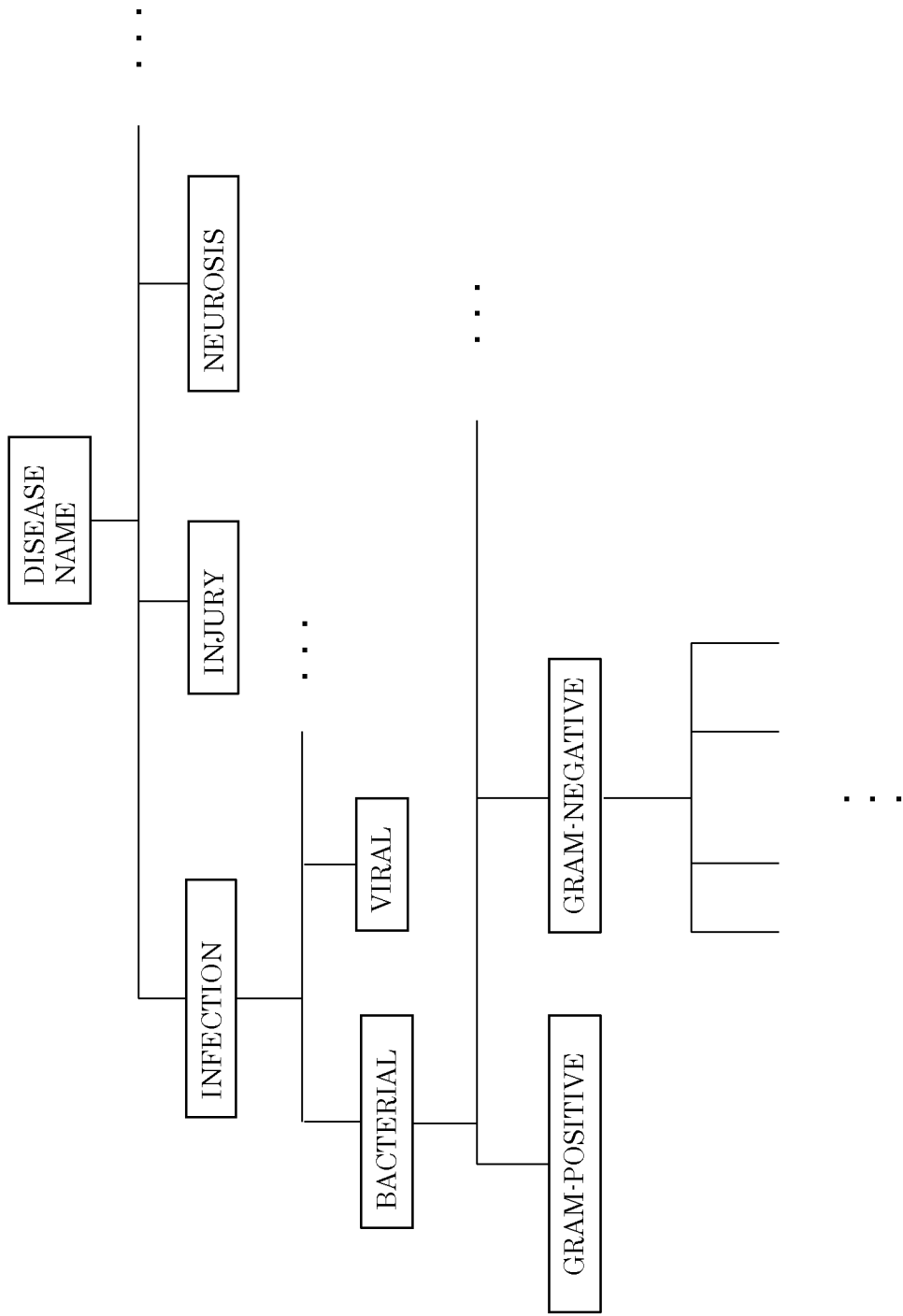
FIG. 3 is a diagram showing disease information recording means.

FIG. 3 is a diagram showing the disease information recording means.

Many disease names and class names grouping the disease names (disease entries) are recorded in a tree structure.

Each disease entry is recording the attributes thereof (disease entry attribute recording means). Also, the disease entries are connected by links representing the parent-child relationships between the disease entries (disease entry parent-child relationship link means) in a tree structure so that the attributes recorded in the disease entry attribute recording means of a parent are inherited to the disease entry attribute recording means of a child (disease entry attribute record parent-child inheritance means). Thus, it is only necessary to record the common attributes of the disease entries in a collected manner once.

As a result, the records of the attributes of the disease entries are structured. That is, complete records are made in the minimum number. Although each disease entry is recording only the minimum number of attributes, it is able to inherit complete attribute records from the parent thereof as necessary.

Also, a disease entry at an appropriate level can be provided to the medicine information recording means through reference link means as a term.

Figure 4:
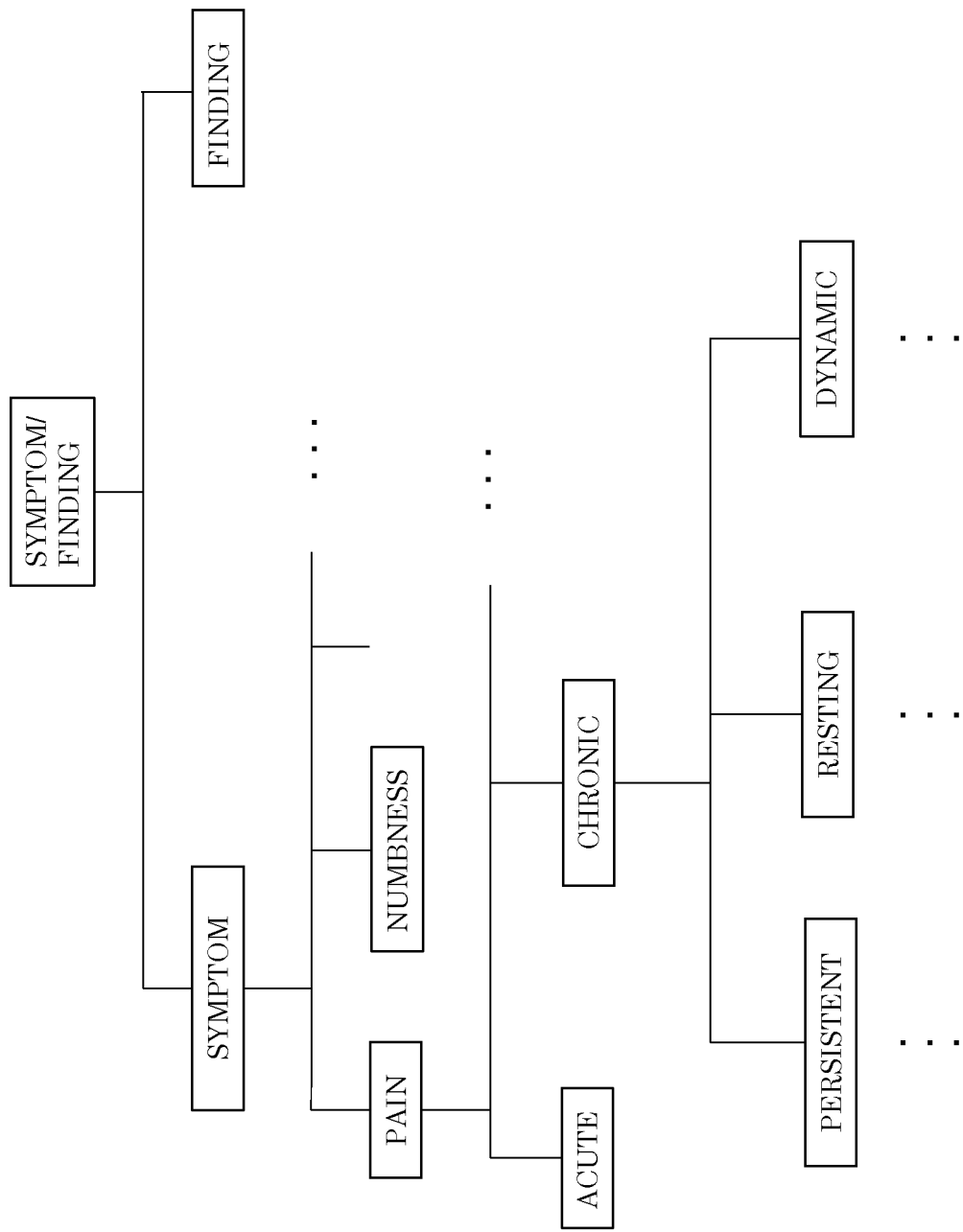
FIG. 4 is a diagram showing symptom/finding information recording means.

FIG. 4 is a diagram showing the symptom/finding information recording means.

Many symptoms and finding names and class names grouping the symptom and finding names (symptom and finding entries) are recorded in a tree structure.

Each symptoms entry or finding entry is recording the attributes thereof (symptom/finding entry attribute recording means). Also, the symptom entries or finding entries are connected by links representing the parent-child relationships between the symptom entries or finding entries (symptom/finding entry parent-child relationship link means) in a tree structure so that the attributes recorded in the symptom/finding entry attribute recording means of a parent are inherited to the symptom/finding entry attribute recording means of a child (symptom/finding entry attribute record parent-child inheritance means). Thus, it is only necessary to record the common attributes of the symptom or finding entries in a collected manner once.

As a result, the records of the attributes of the symptom and finding entries are structured. That is, complete records are made in the minimum number.

Although each symptom or finding entry is recording only the minimum number of attributes, it is able to inherit complete attribute records from the parent thereof as necessary.

Also, a symptom or finding entry at an appropriate level can be provided to the medicine information recording means or disease information recording means through reference link means as a term. Also, the medicine information recording means, disease information recording means, and symptom/finding recording means can provide the entries thereof as terms of the medicine information recording means, disease information recording means, and symptom/finding recording means or the other recording means.

The reference link means of each entry (symptom/finding, disease, or medicine entry) may be the URL of the entry, or may be simply the entry name, which is included in the controlled vocabulary.

The reference link means may be any means as long as information on any entry defined in the symptom/finding, disease, or medicine information recording means is referenced as a term.

Figure 5:
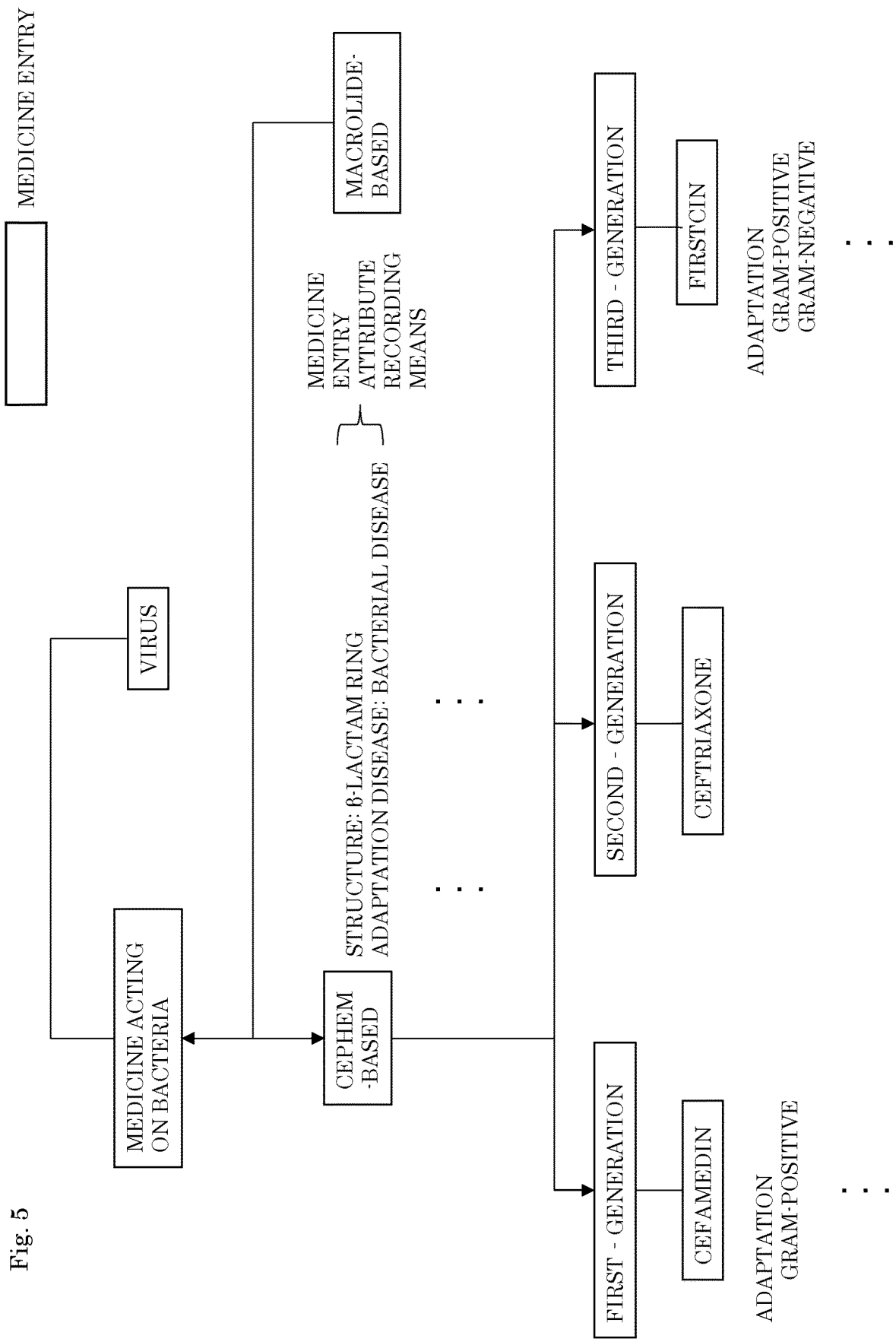
FIG. 5 is a diagram showing the medicine entry attribute record parent-child inheritance means of the medicine information recording means.

FIG. 5 is a diagram showing the medicine entry attribute record parent-child inheritance means of the medicine information recording means.

Medicine entry attribute records such as "structure: β-lactam ring, adaptation disease: bacterial disease," which are the attributes of a parent entry "cephem-based," are inherited to a child medicine entry "Firstcin." Similarly, in the disease information recording means and symptom/finding information recording means, the attribute records of parent entries are inherited to child entries.

Figure 6:
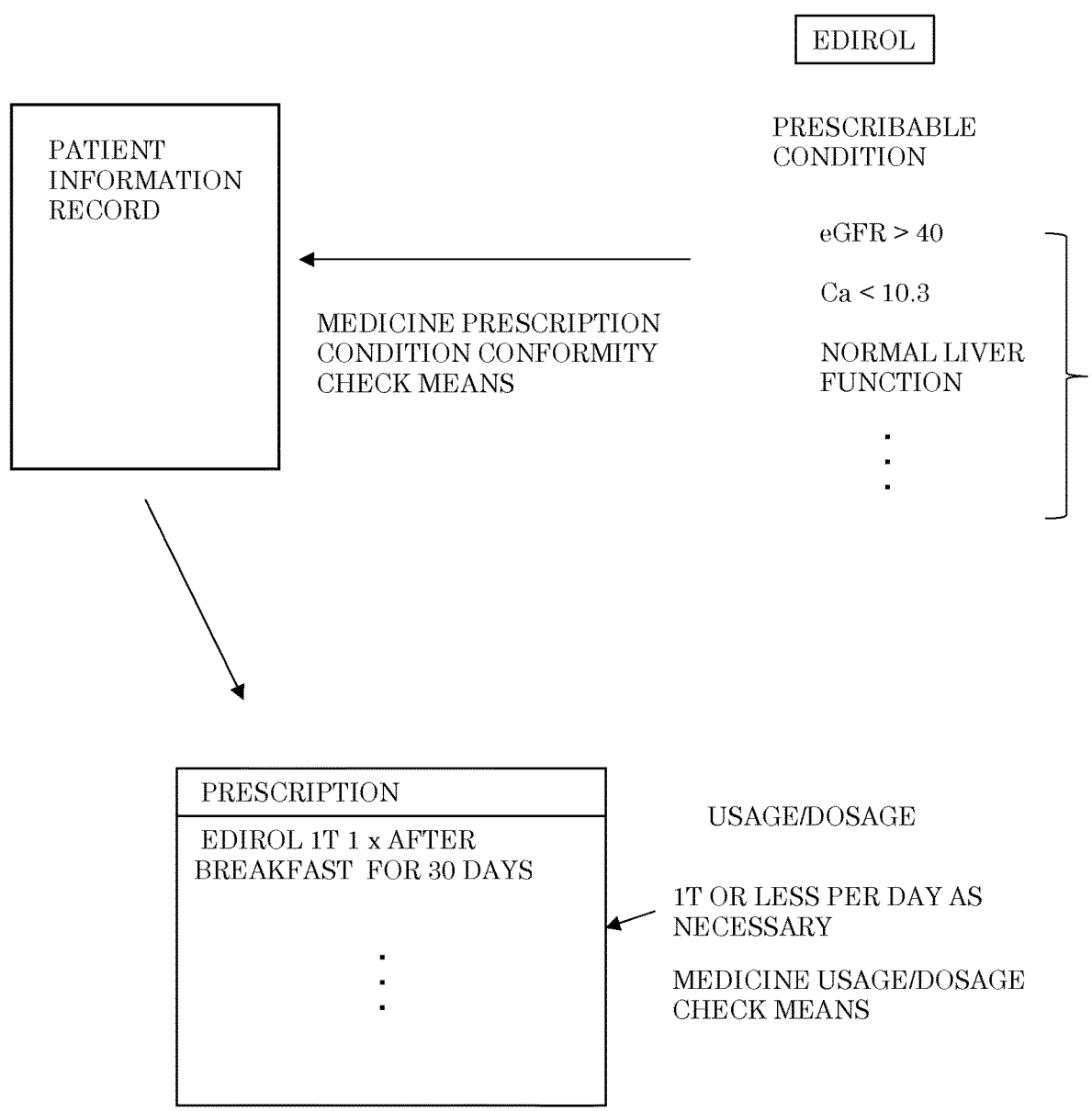
FIG. 6 is a diagram showing prescription condition conformity check means and medicine usage/dosage check means.

FIG. 6 is a diagram showing prescription condition conformity check means and medicine usage/dosage check means.

In a prescription, an adaptation medicine "Edirol" is prescribed against a disease name "osteoporosis" from a patient information record. With respect to this prescription, the medicine usage/dosage check means checks whether the usage and dosage, such as the number of tablets, the number of doses, and daily dose, are specified within respective predetermined ranges. If the usage or dosage deviates from the corresponding predetermined range, it issues a warning.

Also, the medicine prescription condition conformity check means makes, to the patient information record, an inquiry on whether the patient conforms to safe prescription conditions, such as "a predetermined level or more of renal function is present? (eGFR>40)," "hypercalcaemia is not present? (Ca>10.3)," and "normal liver function is being kept?". If the patient does not conform to any safe prescription condition, it issues a warning.

Figure 7:
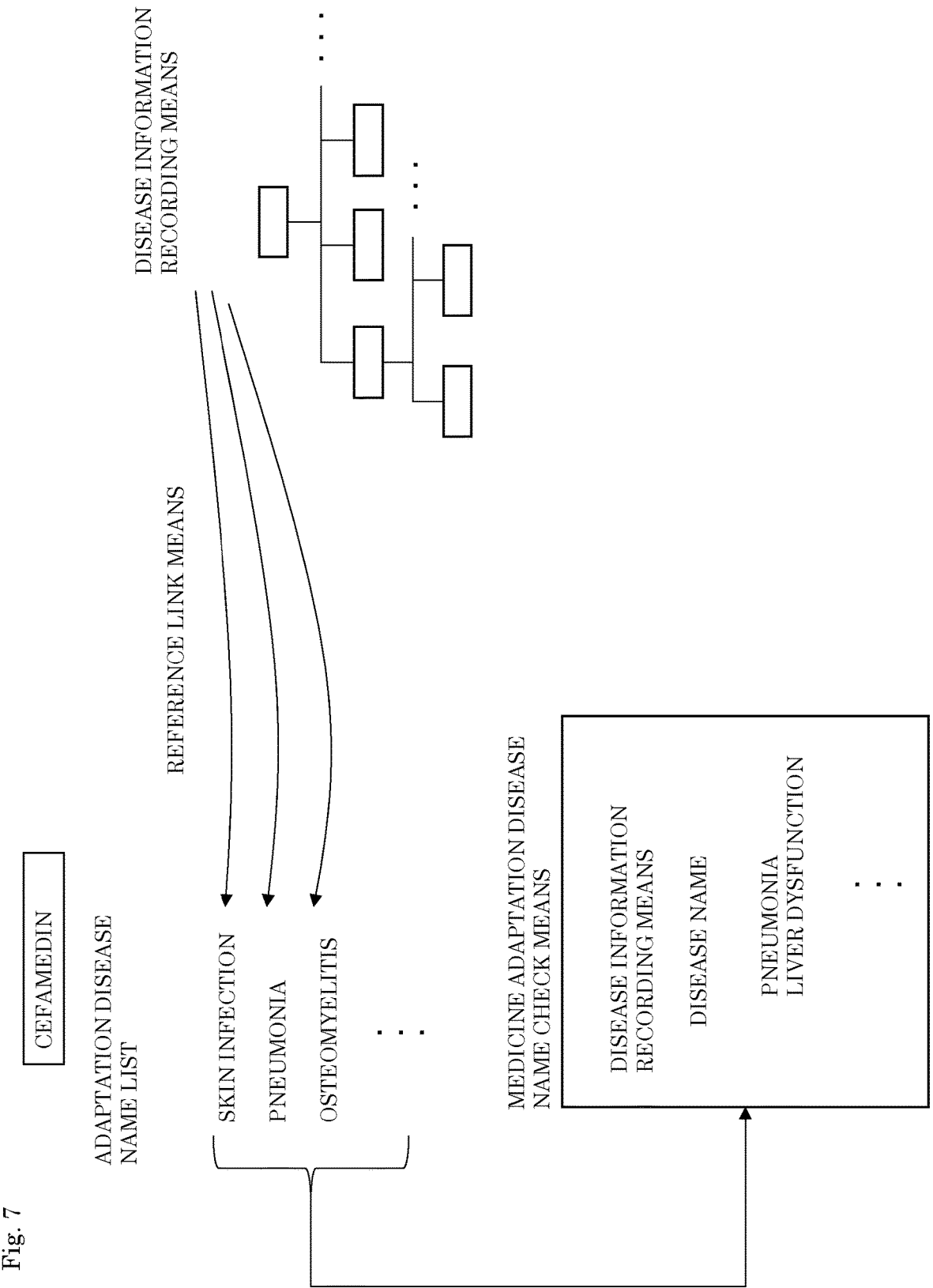
FIG. 7 is a diagram showing adaptation disease name list recording means in the medicine entry attribute recording means and medicine adaptation disease name check means based thereon.

FIG. 7 is a diagram showing adaptation disease name list recording means in the medicine entry attribute recording means and medicine adaptation disease name check means based thereon.

The medicine entry attribute recording means of a medicine entry (in the case of FIG. 7, "Cefamedin") is recording an adaptation diseases name list (medicine adaptation disease name list recording means).

The disease entries in the disease information recording means are used as terms in the list of adaptation disease names through reference link means.

When the medicine adaptation disease name check means searches a disease name list in the patient information record of a prescribed patient and there is no diagnosis name corresponding to the adaptation disease name list, it issues a warning so that an adaptation disease name is registered in the patient information record.

At this time, it is more efficient to present the adaptation disease name list to the prescribing doctor so that the prescribing doctor can select among the disease names in the list.

Each disease entry attribute recording means includes adaptation medicine name list recording means that is recording a list of adaptation medicine names against a disease corresponding to the disease entry attribute recording means.

Each disease entry attribute recording means also includes disease adaptation medicine list presentation means that presents a list of medicines prescribable for a patient having the disease name through reference link means such that the prescribing doctor can select among the medicines in the list. Thus, the load of the prescribing doctor is reduced.

Figure 8:
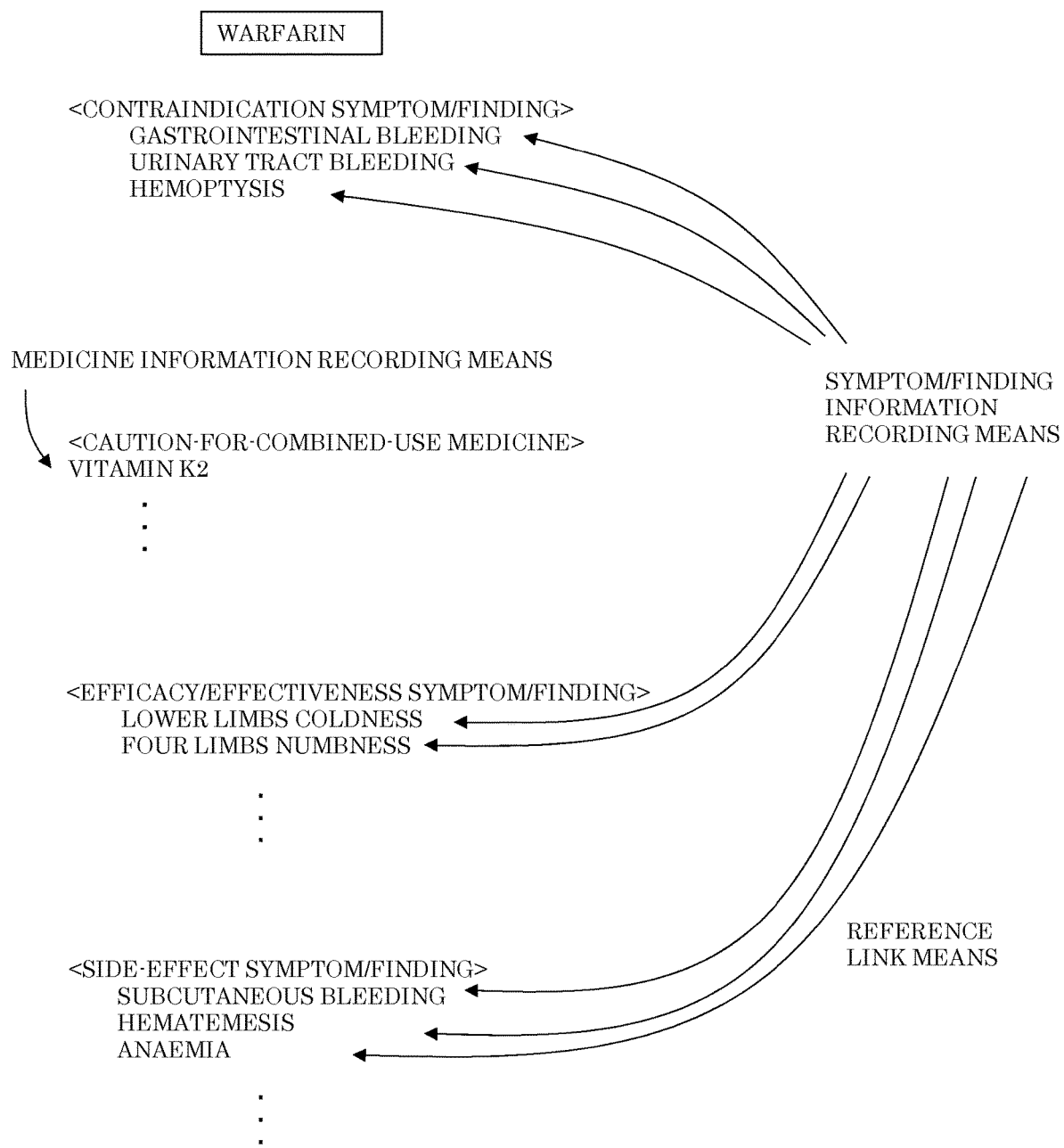
FIG. 8 is a diagram showing contraindication symptom/finding list recording means, caution-for-combined-use medicine list recording means, efficacy/effectiveness symptom/finding recording means, and side-effect symptom/finding recording means in the medicine entry attribute recording means.

FIG. 8 is a diagram showing contraindication disease name list recording means, contraindication symptom/finding list recording means, caution-for-combined-use medicine list recording means, efficacy/effectiveness symptom/finding recording means, and side-effect symptom/finding recording means in the medicine entry attribute recording means.

The disease entries of the disease information recording means are used as terms in a contraindication disease name list through reference link means.

FIG. 8 shows gastrointestinal bleeding such as gastric ulcer, urinary tract bleeding such as bladder bleeding, hemoptysis associated with pulmonary tuberculosis or lung cancer, and the like.

The symptom and finding entries of the symptom/finding information recording means are used as terms in a contraindication symptom or finding list through reference link means. Similarly, symptom and finding entries of the symptom/finding information recording means are used as terms in an efficacy/effectiveness symptom/finding list and a side-effect symptom/finding list.

The medicine entries of the medicine information recording means are used as terms in a caution-for-combined-use medicine list through reference link means.

Each medicine entry attribute recording means includes contraindication symptom/finding list recording means that is recording a list of contraindication symptoms and findings that contraindicate prescription of a medicine corresponding to the medicine entry attribute recording means or contraindication disease name list recording means that is recording a contraindication disease list and caution-for-combined-use medicine list recording means.

Each medicine entry attribute recording means also includes medicine contraindication symptom/finding check means, medicine contraindication disease name check means, and caution-for-combined-use medicine check means that check whether a contraindication symptom or finding, contraindication disease name, or caution-for-combined-use medicine is present in the patient information record of a patient to which the medicine is prescribed, through reference link means and, if present, issues a warning. Thus, a medical accident can be prevented.

Each medicine entry attribute recording means also includes efficacy/effectiveness symptom/finding recording means that is recording a list of symptoms and findings against which the medicine has efficacy and effectiveness and side-effect symptom/finding recording means that is recording a list of side-effect symptoms and findings that may be caused by the medicine.

Each medicine entry attribute recording means also checks whether an efficacy/effectiveness symptom or finding or side-effect symptom or finding is present in the patient information record of a patient to which the medicine has been prescribed, through reference link means. If no efficacy/effectiveness symptom or finding is present (medicine efficacy/effectiveness symptom/finding check means), or if a side-effect symptom or finding is present (medicine side-effect symptom/finding check means), it issues a warning. Thus, prescription of a medicine that has already become unnecessary can be canceled, or a side effect can be prevented from becoming serious, for example, by detecting the side effect early or canceling the causative medicine.

Figure 9:
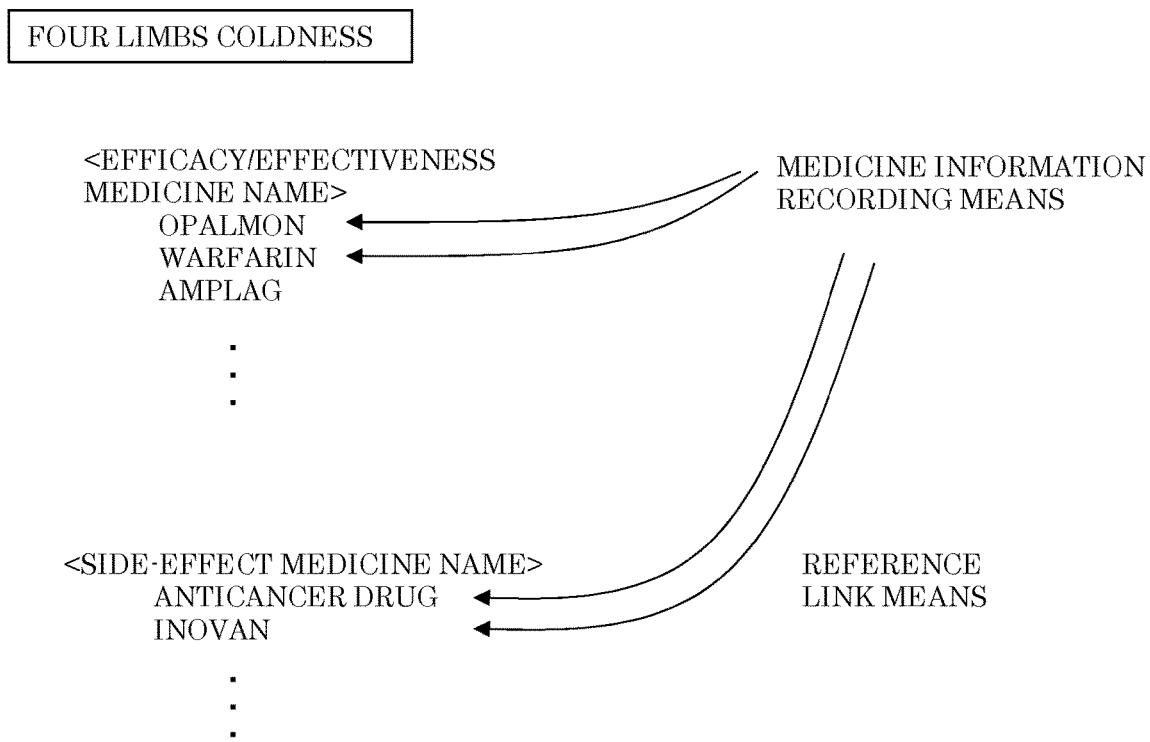
FIG. 9 is a diagram showing efficacy/effectiveness medicine names and side-effect medicine names in each symptom/finding entry attribute recording means of the symptom/finding information recording means.

FIG. 9 is a diagram showing efficacy/effectiveness medicine names and side-effect medicine names in each symptom/finding entry attribute recording means of the symptom/finding information recording means.

Symptoms and findings include symptoms and findings to be treated in association with diseases and symptoms and findings acting as the side effects of medicines.

An attribute "efficacy/effectiveness medicine names" is recording a list of medicine names that have efficacy and effectiveness against symptoms and findings to be treated in association with diseases.

Thus, when treating a disease, medicines having efficacy and effectiveness against an occurring symptom or finding are presented by this list (symptom/finding efficacy medicine list presentation means).

Also, an attribute "side effect medicine names" is recording a list of medicines names that can be used when the symptom or finding is a side effect.

When considering the possibility of a side effect, medicines that may be causing the current symptom or finding are presented by this list (symptom/finding side effect medicine list presentation means).

FIG. 10 is a diagram showing adaptation disease-specific prescription frequency recording means, efficacy/effectiveness symptom/finding-specific prescription frequency recording means, and side-effect symptom/finding-specific prescription frequency recording means in the medicine entry attribute record.

At the time point when prescription of a medicine corresponding to the medicine entry attribute record against an adaptation disease is confirmed, the frequency of prescription against this disease is counted up (disease-specific medicine prescription frequency recording means).

Thus, when prescribing this medicine next time, a list of adaptation disease names is presented in the descending order of the prescription frequency of the medicine (frequency descending order medicine adaptation disease name presentation means). This allows a prescribing doctor to grasp diseases against which this medicine has been prescribed.

Similarly, at the time point when prescription of this medicine against an efficacy/effectiveness symptom or finding is confirmed, the frequency of prescription against this efficacy/effectiveness symptom or finding is counted up (efficacy/effectiveness symptom/finding-specific medicine prescription frequency recording means).

Thus, when prescribing this medicine next time, a list of adaptation disease names is displayed in the descending order of the prescription frequency of the medicine (frequency descending order efficacy/effectiveness medicine display means). This allows a prescribing doctor to grasp efficacy/effectiveness symptoms and findings against which this medicine has been prescribed.

Also, at the time point when prescription of this medicine against a side-effect symptom or finding is confirmed, the frequency of prescription against this side-effect symptom or finding is counted up (side-effect symptom/finding-specific medicine prescription frequency recording means).

Thus, when prescribing this medicine next time, a list of side-effect symptoms and findings is displayed in the descending order of the prescription frequency of the medicine (frequency descending order medicine side-effect symptom/finding display means). This allows a prescribing doctor to grasp side-effect symptoms and findings that this medicine is more likely to cause.

FIG. 11 is a diagram showing efficacy/effectiveness medicine-specific medicine prescription frequency recording means and side-effect symptom/finding-specific medicine prescription frequency recording means in the symptom/finding entry attribute recording means.

At the time point when prescription of a medicine against an efficacy/effectiveness symptom or finding corresponding to the symptom/finding entry attribute recording means is confirmed, the frequency of prescription of this medicine against this efficacy/effectiveness symptom or finding is counted up (efficacy/effectiveness symptom/finding-specific medicine prescription frequency recording means).

Thus, when prescribing a medicine against this symptom or finding next time, a list of medicines is displayed in the descending order of the frequencies of prescription against the efficacy/effectiveness symptom or finding (frequency descending order efficacy/effectiveness symptom/finding medicine display means). This allows a prescribing doctor to grasp the frequencies with which the medicines have been prescribed against this symptom or finding.

Similarly, at the time point when prescription of a medicine against a side-effect symptom or finding corresponding to the symptom/finding entry attribute recording means the is confirmed, the frequency of prescription of this medicine against this side-effect symptom or finding is counted up (side-effect symptom/finding-specific medicine prescription frequency recording means).

Thus, when prescribing a medicine to this symptom or finding next time, a list of medicines is displayed in the descending order of the frequencies of prescription against this side-effect symptom or finding (frequency descending order side-effect symptom/finding medicine display means). This allows a prescribing doctor to grasp the frequencies with which the medicines have been involved in this side-effect symptom or finding.

FIG. 12 is a diagram showing side-effect symptom/finding-specific combined use medicine combination prescription frequency recording means in the medicine entry attribute recording means.

The side-effect symptom/finding-specific combined use medicine combination prescription frequency recording means is recording the frequencies with which a medicine corresponding to the medicine entry attribute recording means and combined use medicines have been prescribed in combination against side-effect symptoms and findings. The medicine entry attribute recording means also includes combined use medicine combination frequency descending order side-effect symptom/finding medicine presentation means that, when prescription of this medicine against a side-effect symptom or finding is confirmed, counts up the side-effect symptom/finding-specific combined use medicine combination prescription frequency recording means with respect to all combined use medicines and, when there are combined use medicines when considering involvement of this medicine in a side-effect symptom or finding next time, displays a list of medicine names in the descending order of the frequencies of prescription of combinations with the combined use medicines. This allows a prescribing doctor to estimate pathophysiology of the side effect while also considering the interaction between the combined use medicines.

FIG. 13 is a diagram showing side-effect symptom/finding-specific combined use medicine combination prescription frequency recording means in the symptom/finding entry attribute recording means.

The side-effect symptom/finding-specific combined use medicine combination prescription frequency recording means is recording the frequencies with which medicines and combined use medicines have been prescribed in combination against a side-effect symptom or finding. The symptom/finding entry attribute recording means also includes combined use medicine combination frequency descending order side-effect symptom/finding medicine presentation means that, when prescription of the medicine against a side-effect symptom/finding corresponding to medicine names is confirmed, counts up the side-effect symptom/finding-specific combined use medicine combination prescription frequency recording means with respect to all combined use medicines and, when there are combined use medicines when considering involvement of a medicine in this symptom/finding symptom or finding next time, presents a list of medicine names in the descending order of the frequencies of prescription of combinations with the combined use medicines. This allows a prescribing doctor to estimate the condition of the side effect while also considering the interaction with the combined use medicines.

Note that count-up is performed in an entry at an appropriate level in the medicine information recording means, disease information recording means, and symptom/finding information recording means. The counted-up frequencies may be added up in a higher-level entry when necessary.

While an embodiment of the present invention has been described, the specific configuration of the present invention is not limited to the embodiment. Design changes and the like in the embodiment are included in the present invention without departing from the spirit and scope of the invention. The description in the diagrams is only illustrative of the concept. When carrying out the present invention, accurate diagrams can be created on the basis of textbooks, papers, or the like. While, in the present specification, the recording means having a tree structure are provided with respect to medicines, diseases, and symptoms and findings, some or all entries may be arranged in parallel rather than forming a hierarchical structure, in accordance with the use. Also, information on body parts, or the like may be used as a different group of entries in combination. The range in which the frequencies of medicines, diseases, and symptoms and findings are counted up may be limited as necessary. For example, the range may be limited to doctors in charge of target patients, groups such as diagnosis and treatment departments, medical institutions, regions, the entire country, or the like Or, rather than limiting the count-up range, a list of the frequencies in corresponding cases may be presented in the descending order.

The invention claimed is:

1. A medicine prescription assistance system comprising:
   medicine information recording means for recording a plurality of medicine entries comprising medicine names and class names grouping the medicine names;
   disease information recording means for recording a plurality of disease entries comprising disease names and class names grouping the disease names; and
   symptom/finding information recording means for recording a plurality of symptom and finding entries comprising symptom and finding names and class names grouping the symptom and finding names, wherein
   the medicine information recording means is configured to record attributes about the medicine entries and to record parent-child relationships between the medicine entries by linking them in a tree structure, such that attribute records of a parent medicine entry are inherited by attribute records of a child medicine entry;
   the disease information recording means is configured to record attributes about the disease entries and to record parent-child relationships between the disease entries by linking them in a tree structure, such that attribute records of a parent disease entry are inherited by attribute records of a child disease entry; and
   the symptom/finding information recording means is configured to record attributes about the symptom and finding entries and to record parent-child relationships between the symptom and finding entries by linking them in a tree structure, such that attribute records of a parent symptom and finding entry are inherited by attribute records of a child symptom and finding entry; and
   the medicine prescription assistance system further comprising reference link means through which each of the entries is mutually referenced as terms in respective recording means, using URLs;
   a list of adaptation disease names against which a medicine is allowed to be prescribed is recorded,
   in response to the medicine being prescribed to a patient, whether there is an adaptation disease name in a patient information record of the patient is checked, and
   in response to there being no adaptation disease name, a prescribing person is urged to input an adaptation disease.

2. The medicine prescription assistance system of claim 1, wherein:
   a condition under which a medicine is allowed to be prescribed is recorded; and
   in response to prescribing the medicine to a patient, whether a patient information record of the patient conforms to the condition is checked, and
   in response to the patient information record not conforming to the condition, a warning is issued to a prescribing person.

3. The medicine prescription assistance system of claim 1, wherein:
   prescribable usage and dosage of a medicine is recorded; and
   in response to the medicine being prescribed to a patient, whether usage and dosage of the medicine conform to the prescribable usage and dosage while referencing a patient information record of the patient as necessary is checked, and
   in response to the usage and dosage not conforming to the prescribable usage and dosage, a warning is issued to a prescribing person.

4. The medicine prescription assistance system of claim 1, wherein:
   a list of adaptation medicine names against a disease is recorded; and
   a list of medicines that are allowed to be prescribed to a patient of the disease is presented through the reference link means.

5. The medicine prescription assistance system of claim 1, wherein:
   a list of contraindication disease names that contraindicate a medicine is recorded; and
   in response to the medicine being prescribed to a patient, whether there is a contraindication disease name in a patient information record of the patient is checked through the reference link means.

6. The medicine prescription assistance system of claim 1, wherein:
   a list of contraindication symptoms and findings that contraindicate a medicine is recorded; and
   in response to the medicine being prescribed to a patient, whether there is a contraindication symptom or finding in a patient information record of the patient is checked through the reference link means.

7. The medicine prescription assistance system of claim 1, wherein:
a list of symptoms and findings against which a medicine has efficacy and effectiveness is recorded; and
in response to the medicine being prescribed to a patient, whether there is a symptom or finding against which the medicine has efficacy and effectiveness, in a patient information record of the patient is checked through the reference link means.

8. The medicine prescription assistance system of claim 1, wherein:
a list of medicine names that have efficacy and effectiveness against a symptom or finding is recorded; and
a list of medicines that have efficacy and effectiveness for a patient having the symptom or finding is presented through the reference link means.

9. The medicine prescription assistance system of claim 1, wherein:
a list of side-effect symptoms and findings that may be caused by a medicine is recorded; and
in response to the medicine being prescribed to a patient, whether there is a side-effect symptom or finding in a patient information record of the patient is checked through the reference link means.

10. The medicine prescription assistance system of claim 1, wherein:
a list of medicine names that may cause a symptom or finding as a side effect is recorded; and
a list of medicines that may cause a side effect, to a medicine prescription list of a patient having the symptom or finding is presented through the reference link means.

11. The medicine prescription assistance system of claim 1, wherein:
frequencies with which a medicine has been prescribed against diseases are recorded; and
in response to a disease name corresponding to medicine names being confirmed, the frequencies are counted up, and
in response to the medicine being prescribed next time, a list of adaptation disease names in the descending order of the frequencies of prescription is displayed.

12. The medicine prescription assistance system of claim 4, wherein:
frequencies with which medicines have been prescribed against a disease are recorded; and
in response to a disease name corresponding to medicine names being confirmed, the frequencies are counted up, and
in response to a medicine being prescribed against the disease next time, a list of adaptation medicine names in the descending order of the frequencies of prescription is displayed.

13. The medicine prescription assistance system of claim 7, wherein:
frequencies with which the medicine has been prescribed against efficacy/effectiveness symptoms and findings are recorded; and
in response to an efficacy/effectiveness symptom or finding corresponding to medicine names being confirmed, the frequencies are counted up, and
in response to the medicine being prescribed next time, a list of efficacy/effectiveness symptoms and findings in the descending order of the frequencies of prescription is presented.

14. The medicine prescription assistance system of claim 8, wherein:
frequencies with which medicines have been prescribed against the efficacy/effectiveness symptom or finding are recorded; and
in response to an efficacy/effectiveness symptom or finding corresponding to medicine names being confirmed, the frequencies are counted up, and
in response to a medicine being prescribed against the efficacy/effectiveness symptom or finding next time, a list of medicine names in the descending order of the frequencies of prescription is displayed.

15. The medicine prescription assistance system of claim 9, wherein:
frequencies with which the medicine has been prescribed against side-effect symptoms and findings are recorded; and
in response to prescription of the medicine against a side-effect symptom/finding corresponding to medicine names being confirmed, the frequencies are counted up, and
in response to the medicine being prescribed next time, a list of side-effect symptoms and findings in the descending order of the frequencies of prescription is presented.

16. The medicine prescription assistance system of claim 9, wherein:
frequencies with which the medicine and combined use medicines have been prescribed in combination against side-effect symptoms and findings and combined use medicine combination are recorded; and
in response to prescription of the medicine against a side-effect symptom/finding corresponding to medicine names being confirmed, the frequencies are counted up, and
in response to there being a combined use medicine,
in response to prescribing the medicine next time, a list of side-effect symptoms and findings in the descending order of the frequencies of combined use medicine combination prescription is presented.

17. The medicine prescription assistance system of claim 10, wherein:
frequencies with which medicines have been prescribed against the side-effect symptom or finding are recorded; and
in response to prescription of the medicine against a side-effect symptom/finding corresponding to medicine names being confirmed, the frequencies are counted up, and
in response to considering involvement of a medicine in the side-effect symptom or finding next time, a list of medicine names in the descending order of the frequencies of prescription is presented.

18. The medicine prescription assistance system of claim 10, wherein:
frequencies with which medicines and combined use medicines have been prescribed in combination against the side-effect symptom or finding and combined use side-effect symptom/finding medicine combination are recorded; and
in response to prescription of the medicine against a side-effect symptom/finding corresponding to medicine names being confirmed, the frequencies are counted up,
in response to there being a combined use medicine, and
in response to considering involvement of a medicine to the side effect symptom or finding next time, a list of medicine names in the descending order of the frequencies of combined use medicine combination prescription is presented.

\* \* \* \* \*